United States Patent
Del Toro et al.

[11] Patent Number: 5,788,707
[45] Date of Patent: *Aug. 4, 1998

[54] PULL BACK SLEEVE SYSTEM WITH COMPRESSION RESISTANT INNER SHAFT

[75] Inventors: Connie Del Toro, Plymouth; Dean A. Peterson, Minneapolis; Susan M. Shoemaker, Elk River, all of Minn.

[73] Assignee: Scimed Life Systems, Inc., Maple Grove, Minn.

[*] Notice: The portion of the term of this patent subsequent to May 18, 2015, has been disclaimed.

[21] Appl. No.: 484,006

[22] Filed: Jun. 7, 1995

[51] Int. Cl.$^6$ .................................................. A61F 11/00
[52] U.S. Cl. ........................... 606/108; 606/195; 606/198
[58] Field of Search ................................ 606/108, 198, 606/191, 195; 623/1

[56] References Cited

U.S. PATENT DOCUMENTS

| | | |
|---|---|---|
| 4,733,665 | 3/1988 | Palmaz . |
| 4,776,337 | 10/1988 | Palmaz . |
| 4,795,458 | 1/1989 | Regan ........................................ 623/1 |
| 4,848,343 | 7/1989 | Wallsten et al. . |
| 4,950,227 | 8/1990 | Savin et al. . |
| 5,026,377 | 6/1991 | Burton et al. . |
| 5,104,399 | 4/1992 | Lazarus ........................................ 623/1 |
| 5,158,548 | 10/1992 | Lau et al. . |
| 5,160,341 | 11/1992 | Brenneman et al. . |
| 5,192,297 | 3/1993 | Hull . |
| 5,195,984 | 3/1993 | Schatz . |
| 5,201,757 | 4/1993 | Heyn et al. . |
| 5,242,399 | 9/1993 | Lau et al. . |
| 5,338,295 | 8/1994 | Cornelius et al. . |
| 5,344,426 | 9/1994 | Lau et al. . |
| 5,360,401 | 11/1994 | Turnland . |
| 5,395,332 | 3/1995 | Ressemann et al. ................ 604/280 |
| 5,417,708 | 5/1995 | Hall et al. ........................... 606/108 |

FOREIGN PATENT DOCUMENTS

| | | |
|---|---|---|
| 0505686A1 | 9/1992 | European Pat. Off. . |
| 0 556 940 A1 | 8/1993 | European Pat. Off. . |
| 0611556A1 | 9/1994 | European Pat. Off. . |
| 219257A | 3/1988 | United Kingdom . |
| WO86/03398 | 6/1986 | WIPO . |
| WO 93/11823 | 6/1993 | WIPO . |
| WO 96/13228 | 5/1996 | WIPO . |

*Primary Examiner*—Michael A. Brown
*Assistant Examiner*—Justine R. Yu
*Attorney, Agent, or Firm*—Vidas, Arrett & Steinkraus, P.A.

[57] ABSTRACT

A stent delivery system for delivering a stent comprising, a stent disposed on the distal end of the catheter, and an inner core, wherein the inner core is resistant to appreciable compression or accordion. The catheter further comprising a first sheath covering a portion of the inner core, wherein at least a portion of the distal end of the inner core is left uncovered by the first sheath, a retractable sheath which covers at least a portion of the stent and a portion of the distal end of the inner core and a retracting means for retracting the distal sheath to release the stent.

16 Claims, 4 Drawing Sheets

PULL BACK SLEEVE SYSTEM WITH COMPRESSION RESISTANT INNER SHAFT

FIELD OF THE INVENTION

This invention relates to a stent delivery catheter system, such as the kind used in percutaneous transluminal coronary angioplasty (PTCA) procedures. More particularly, it relates to a stent delivery catheter employing a novel retractable protective sheath and a compression resistant inner shaft, and to a method of making the retractable protective sheath.

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon catheter could be used. This device features a guide wire which is affixed to the catheter and cannot be removed.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is pulled back to expose the stent. After the sheath is removed, the stent is free to expand or be expanded. Such stent delivery catheters have had problems with the integrity of the inner core and the outer sheath. In a normal pull back system the friction encountered when pulling the distal sheath off of the stent causes the innermost shaft to compress or accordion and the outermost sheath to elongate. This increases the likelihood of the inner core collapsing and the failure of the device to deploy the stent.

The present invention is directed toward remedying this collapsing or accordion type failure of the inner core. The invention is also directed toward an improved sheath and a method of making a low friction, strong, flexible sheath to be used in the stent delivery catheter.

SUMMARY OF THE INVENTION

The present invention provides an improved stent delivery catheter. The catheter includes a stent disposed on the distal end of the catheter, an inner core, which is flexible and resistant to appreciable compression or accordion, and an outer sheath covering a majority of the inner core, excluding at least a portion of the distal end of the inner core. The catheter further comprises a retractable distal sheath which covers at least a portion of the stent and a portion of the distal end of the inner core and a retracting means for retracting the distal sheath to release the stent.

The present invention further provides a retractable distal sheath and a method for making said retractable distal sheath. The inventive method comprises: placing a sheath comprising tetrafluoroethylene fluorocarbon polymers (TFEF) or fluorinated ethylene-propylene resins (FEP), such as Teflon™, on a mandrel, and winding a wire coil around the sheath. The sheath or tubing is then heated, allowing the tubing to soften and the wire coil to create grooves in the soft tubing. After a certain period of heating, the tubing is allowed to cool and the mandrel and wire coil are removed. The resulting sheath demonstrates increased flexibility, sufficient strength and a low coefficient of friction.

Other objects, features, and characteristics of the present invention, as well as the methods of operation and functions of the related elements of the structure, and the combination of parts and economics of manufacture, will become more apparent upon consideration of the following description with reference to the accompanying drawings, all of which form a part of this specification.

DETAILED DESCRIPTION OF THE INVENTION

Figure 1:
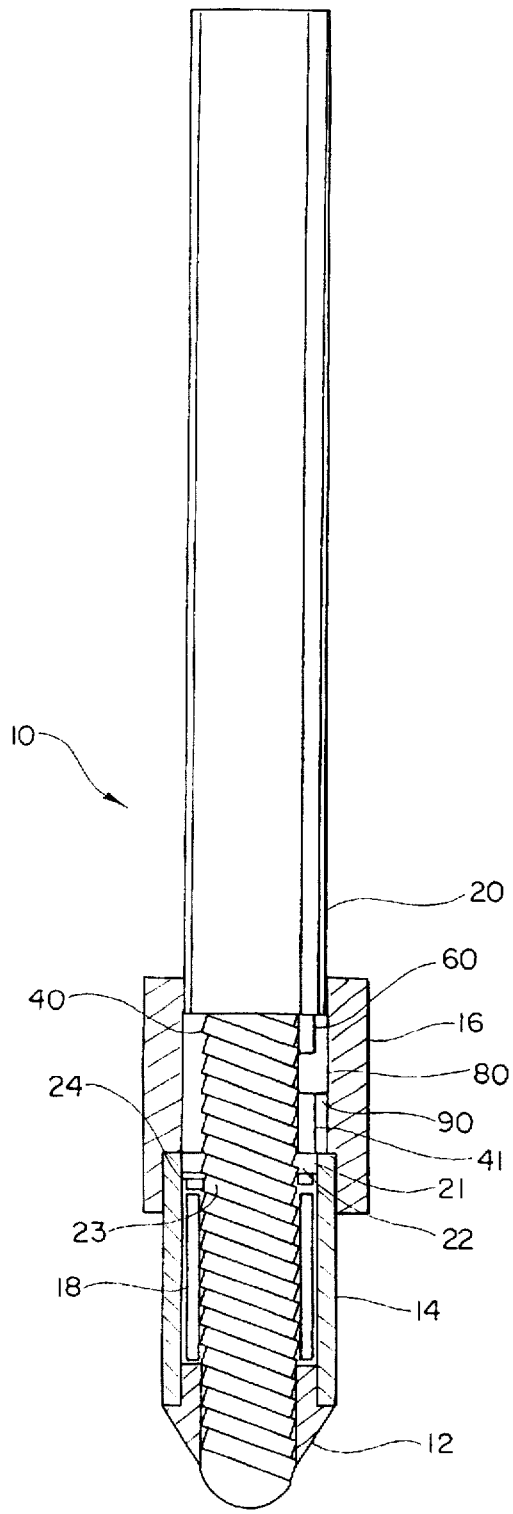
FIG. 1 shows a side view of a catheter according to the invention including a cross-sectional view of the distal portion thereof.

In FIG. 1 there is shown a cross-section of the distal portion of a specific embodiment of a stent delivery catheter generally designated as 10. The device generally comprises an outer sheath 20 which covers the majority of the catheter excluding a portion of the distal end of the catheter. This sheath 20 is characterized by a low friction coefficient and high flexibility, and preferably is comprised of a polyolefinic ionomer material, such as a single layer Surlyn™ sheath. The outer sheath 20 surrounds an inner core 40 which extends to the distal tip 12 of the catheter. The inner core is preferably a spring coil 40, the manufacture of which is well known in the art, and is fashioned to be both flexible when navigated through body lumens and rigid when being pulled back upon itself during stent release. The spring coil may be made from a variety of material, including stainless steel, elgiloy, Nitinol™, Kevlar™ or other metals and structural plastics. Preferably, it is made from stainless steel. The present invention further comprises a retractable distal sheath 14 covering a stent 18, which is loaded around the distal end of the inner core 40, and a retracting member 41, which is connected to the retractable distal sheath 14 and allows the physician to retract the distal sheath 14 from the proximal end of the catheter. The retractable sheath 14 may be flexible or rigid, and is generally used to protect stent 18 and the vessel wall and/or to hold a self-expanding stent in the delivery configuration. The distal sheath 14 and the method for making it are discussed further below. The retracting member 41 may be a rod, a tube, a pull back wire or the like, but is preferably a wire. The retracting member 41 extends proximally through the outer sheath 20, preferably through a retracting member lumen 80, such as a tube preferably made from high density polyethylene (HDPE), but which could also be made from low density polyethylene (LDPE), polyimide, Teflon™ or other lubricious shaft material. In the preferred embodiment, the retracting member lumen 80 extends longitudinally under the outer sheath 20, and houses the pull back wire 41. The retracting member lumen 80 that houses the pull back wire 41 may also carry flushing fluid for purging and cleaning the catheter at the distal end. Retracting member 41 exits the retracting member lumen 80 at exit hole 90, and continues distally to where it is attached to the distal sheath at point 21. The invention additionally comprises a proximal sheath 16 which covers the exposed area between the outer sheath 20 and the distal sheath 14, serving to protect the inner core 40 and the retracting member 41 in this area. The proximal sheath 16 is adhered to the proximal end of the distal sheath 14 and slidably overlaps the distal end of the outer sheath 20. As the distal sheath 14 is retracted, the proximal sheath 16 is forced back, sliding over the outer sheath 20 giving the distal sheath room to retract. The distance between the proximal end of the distal sheath 14 and exit hole 90 should preferably be far enough apart to allow complete release of the stent. The distal sheath 14 and the proximal sheath 16 may be two separate sheaths adhered to one another, or they may be combined to form on continuous sheath. Finally, a stiffening wire 60, preferably made from stainless steel, but which could also be made from Nitinol™ or Elgiloy, may also be incorporated longitudinally along the axis of the catheter 10 for extra stability and control.

Figure 2:
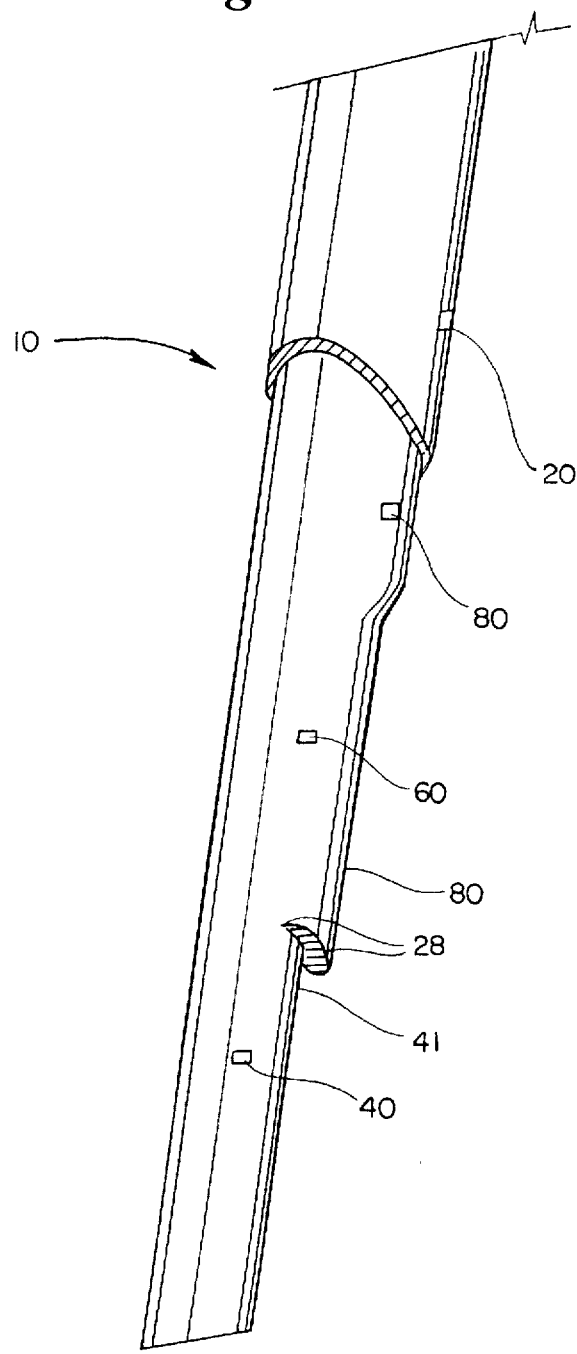
FIG. 2 shows a partial cut away view of a distal portion of a catheter according to the invention.

FIG. 2 shows the layers of the catheter excluding the distal portion of the outer sheath 20, the distal and proximal sheaths and the stent. As shown, the stiffening wire 60 and the retracting member lumen 80, which are positioned longitudinally along the catheter, may be truncated prior to the flexible distal tip. The truncated portion 28 may be terminated at the end of the outer sheath 20 or extend into the gap between the distal end of the outer sheath 20 and the proximal end of the distal sheath 14, as shown in FIG. 1. The retracting member 41 extends out through the truncated lumen 28 connecting with the distal sheath 14.

In the preferred embodiment, the distal sheath 14 is connected via a short section of hypotube 22, configured as an annular ring, to the pull back wire 41. The proximal end of the distal sheath 14 is adhered to the annular ring 22 and the pull back wire 10 is connected, preferably welded, to the inside of the annular ring 22. Proximal to the placement of the stent 18 is a stopper 24. The stopper 24 is usually a piece of tubing attached at position 23 to the inner core, and is used to prevent the stent 18 from moving proximally when the distal sheath 14 is pulled back over the stent 18.

Figure 3:
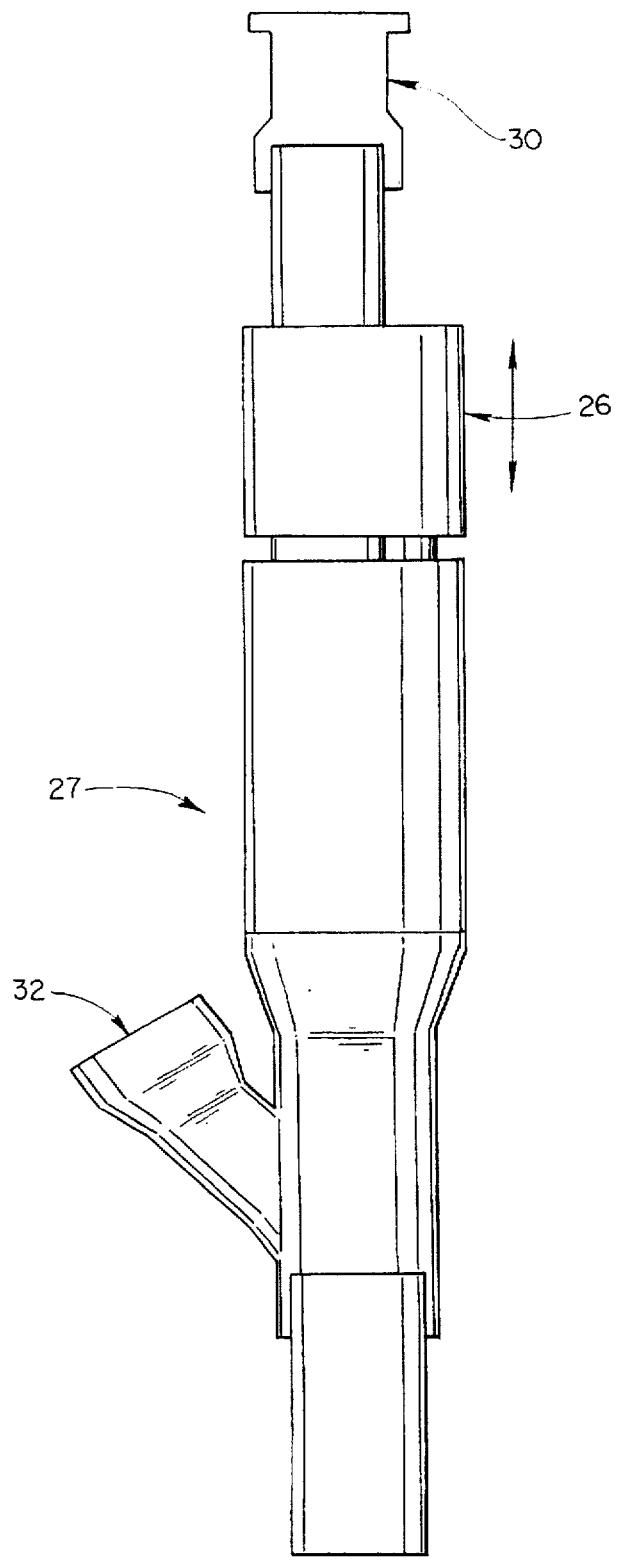
FIG. 3 shows a side view of the proximal end of a catheter according to the invention showing the manifold portion thereof.
Figure 4A:
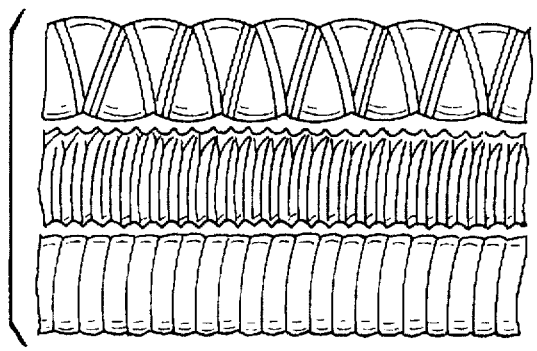
FIGS. 4a–4d show side views of optional contour patterns for the retractable distal sheath of the invention.
Figure 4B:
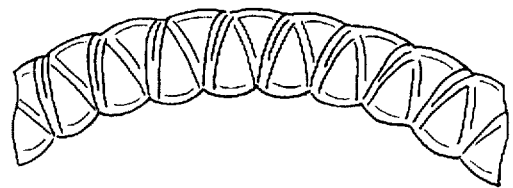
Figure 4C:
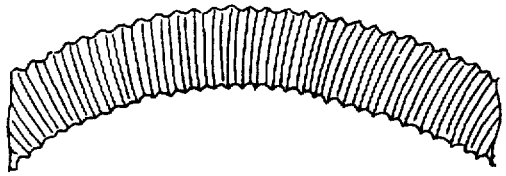
Figure 4D:
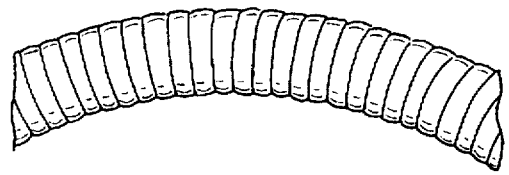

The proximal portion of the catheter, as shown in FIG. 3, comprises of a manifold system 27 which includes a sliding member 26 slidably integrated between the distal end of the manifold and the proximal Luer fitting 30. It is connected to the pull back wire 41 by a weld, insert mold or other connection means. By sliding the sliding member 26 of the manifold 27, distal to proximal, the distal sheath 14 is retracted exposing the stent 18. The manifold 27 may further comprise a hydrating luer 32, which is located on the distal end of the manifold 27 and is used to hydrate the distal tip 12.

The inner core 40 is a non-compressible inner shaft that resists collapse or accordion type failure during the retraction of the distal sheath 14. In the preferred embodiment, a spring coil, most preferably a 6-fillar spring coil, is utilized for the inner core of the delivery device. A spring coil 40 such as used in the present invention provides both flexibility during placement and rigidity during distal sheath retraction. The spring coil 40 allows the delivery system to deploy the stent 18 despite the amount of friction encountered at the distal end resulting from the use of a self expanding stent 18. As the wire 41 is pulled back to expose the self expanding stent 18, the spring coil 40 will collapse slightly upon itself until the excess pitch has been taken up. Once this has happened, the spring coil 40 behaves as a rigid solid structure and therefore will not accordion, providing enough structural support for the distal sheath 14 to be pulled back and expose the self expanding stent 18.

To prepare the stent delivery catheter 10 the stent 18 is compressed and loaded on the distal end of the inner core 40 inside of the distal sheath 14. The stent 18 is surrounded by protective distal sheath 14. The distal sheath remains covering the underlying stent during the placement of the stent 18 by the delivery catheter 10 through the patient's vasculature. During the placement of the stent, protective distal sheath 14 protects the patient's vasculature from the stent 18. When it is time to expand the stent 18 into an enlarged diameter form and secure the stent in a patient's vasculature, the distal sheath 14 is retracted from over stent 18 by sliding the sliding member 26 proximally. As the sliding member is pulled back the distal sheath 14 starts to retract. Once the stent 18 is dragged slightly back by the retracting distal sheath and is butted up against the stopper 24, the stent 18 expands fully as the distal sheath 14 continues to be pulled back. Preferably the stent is self expanding, such as a well known Nitinol™ stent, or it may be expanded by means of an optional internal balloon (not shown) positioned under the stent on the distal end of the inner core 40, as is well known in the art. Once the sheath 14 is fully retracted the optional placement balloon would be inflated through its inflation lumen (not shown) to deploy the stent. After the stent is expanded and in place, the catheter is withdrawn.

The stent deployment catheter preferably incorporates a distal sheath material covering the stent with the following characteristics: low coefficient of friction to slide over the stent, which may comprise collagen material coating or bare metal, radial strength in order to hold down the self expanding stent and high flexibility to maneuver through torturous vasculature. Sheaths comprising tetrafluoroethylene fluorocarbon polymers (TFEF) or fluorinated ethylene-propylene resins (FEP), such as Teflon™, have been found by the inventor to have the least amount of friction when dragged against the stent and inner core, while providing adequate radial strength to hold the stent in place. However, the TFEF/FEP sheaths have thick walls and make the distal tip too stiff for use in the peripheral anatomy. The present invention contemplates using TFEF/FEP sheaths as the distal sheath, or both the distal sheath and the proximal sheath, of the stent deployment catheter and a new method of making the thick TFEF/FEP sheaths more flexible for use in a tortuous anatomy.

In making the desired distal sheath, a standard piece of Teflon™ tubing is placed on a mandrel just slightly smaller than the tubing's inner diameter. Using a coil winder, a wire coil is wound directly over the tubing advancing from one end to the other end, noting the pitch and tension of the wire as the coil is laid on top of the Teflon™ tubing. The wire chosen can be either a round cross section or a rectangular cross section, preferably round with a diameter between 0.005"–0.015". Heat is applied circumferentially to the coil wound tubing, at about 375° C.–450° C., preferably 420° C. The tubing is then allowed to cool to approximately room temperature and the spring coil and the mandrel are removed from the tubing leaving a contoured tube. The coil winder used to create the contoured surface may e wound to produce a variety of contour patterns. FIGS. 4a–4d illustrate possible configurations. The amount of flexibility can be controlled by varying the amount of tension on the wire, the size of the wire, the wire profile, and the pitch of the wire. Preferably, a pitch of 0.010"–0.075" is utilized.

This type of heat method provides a contoured surface on the Teflon™ sheath which results in a measurably improved retractable sheath having increased flexibility and sufficient strength. During heating, the tension from the hot wire leaves grooves in the softened tubing which allow the tubing to be more flexible. The resultant increase in flexibility is by approximately seven times when compared to the original piece of tubing, while still providing enough radial strength to hold down the stent as well as providing the needed lubricity to remove the sheath from the stent. While fluorinated polymers are preferred, any thermoformable polymer may be employed.

The contouring process may also be used to provide flexible shafts for other medical devices such as balloon catheters or infusion catheters, or for any other devices in which a flexible shaft is needed. In an infusion catheter, flexibility could be provided by contouring the distal end of the device. In a balloon catheter, the contouring could be used on either the inflation lumen or guidewire lumen as it would provide for fluid containment while providing flexibility.

The above disclosure is intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent delivery system comprising:
   a substantially incompressible inner core having proximal and distal ends;
   a stent concentrically arranged around the inner core near the distal end;
   an outer sheath concentrically arranged around the inner core and positioned along the inner core proximal to the stent;
   a retractable distal sheath concentrically arranged around the inner core toward the distal end thereof, the retractable distal sheath surrounding at least a portion of the stent and being positioned along the inner core distal to the outer sheath, such that the retractable distal sheath is slidably movable along the inner core and relative to the outer sheath and wherein the retractable distal sheath and a portion of the distal end of the outer sheath are overlapping; and
   retracting means extending from the proximal end of the stent delivery system toward the distal end, and being connected to the retractable distal sheath for retracting the retractable distal sheath proximally toward the outer sheath such that the retracting means moves axially with respect to the outer sheath,
   whereby when the retracting means is retracted the retractable distal sheath is retracted freeing the stent for delivery.

2. The stent delivery system as in claim 1, wherein the inner core comprises a spring coil having a predetermined pitch such that it is flexible in an uncompressed state, and will become rigid when compressed.

3. The stent delivery system as in claim 1, wherein the retracting means comprises a pull back wire attached to the retractable distal sheath, the pull back wire being longitudinally moveable.

4. The stent delivery system as in claim 3, further comprising an annular ring, wherein the pull back wire is attached to the annular ring and wherein the retractable distal sheath is adhered to the annular ring allowing the pull back wire to retract the retractable distal sheath.

5. The stent delivery system as in claim 4, further comprising a stopper attached to the inner core and positioned to prevent the stent from moving proximally as the retractable distal sheath is retracted to expose the stent.

6. The stent delivery system as in claim 5, further comprising a pull back wire lumen which partially encloses the pull back wire and is at least partially covered by the outer sheath.

7. The stent delivery system as in claim 6, further comprising a stiffening wire having proximal and distal ends positioned longitudinally along the inner core.

8. The stent delivery system as in claim 7, wherein the distal end of the stiffening wire and the distal end of the pull back wire lumen are truncated prior to the annular ring.

9. The stent delivery system as in claim 4, wherein the retractable distal sheath comprises a proximal sheath having proximal and distal ends, the proximal end of the proximal sheath overlapping the distal end of the outer sheath, and a distal sheath having proximal and distal ends, the distal end of the proximal sheath being connected to the proximal end of the distal sheath and wherein the annular ring is attached to the proximal end of the distal sheath.

10. The stent delivery system as in claim 9, further comprising a manifold at the proximal end of the stent delivery system, the manifold comprising a sliding member which is connected to the pull back wire and acts to retract said pull back wire.

11. The stent delivery system as in claim 10, wherein the outer sheath comprises polyolefinic ionomer material.

12. The stent delivery system as in claim 11, wherein the retractable distal sheath is made of material which comprises tetrafluoroethylene fluorocarbon polymers or fluorinated ethylene-propylene resins.

13. The stent delivery system as in claim 12, wherein the retractable distal sheath comprises a contoured pattern of grooves.

14. The stent delivery system as in claim 13, further comprising a pull back wire lumen through which the pull back wire extends, the pull back wire having a distal portion which extends out of the pull back wire lumen and attaches to the retractable distal sheath, the pull back wire lumen being in fluid communication with a hydrating luer attached to the manifold.

15. A stent delivery system comprising:
   a substantially incompressible inner core having proximal and distal ends, and being made from a wire coil with a predetermined pitch such that it is flexible in an uncompressed state, and will become rigid when compressed;
   a stent concentrically arranged around the inner core near the distal end;
   an outer sheath concentrically arranged around the inner core and positioned along the inner core proximal to the stent;
   a retractable distal sheath surrounding at least a portion of the stent and being positioned along the inner core distal to the outer sheath, such that the retractable distal sheath is slidably movable along the inner core and relative to the outer sheath and wherein the retractable distal sheath and a portion of the distal end of the outer sheath are overlapping;, and
   retracting means extending from the proximal end of the stent delivery system toward the distal end within the outer sheath, and being connected to the retractable distal sheath for retracting the retractable distal sheath, such that the retracting means moves axially with respect to the outer sheath;

whereby when the retracting means is retracted to free the stent for delivery, the retractable distal sheath is retracted, causing the wire coil to compress, making the wire coil substantially rigid, preventing the inner core from collapsing.

16. A stent delivery system comprising:

a substantially incompressible inner core having proximal and distal ends;

a stent concentrically arranged around the inner core near the distal end;

an outer sheath concentrically arranged around the inner core;

a retractable distal sheath concentrically arranged around and slidably movable along the inner core toward the distal end thereof, the retractable distal sheath surrounding at least a portion of the stent and wherein the retractable distal sheath and a portion of the distal end of the outer sheath are overlapping; and a retracting pull back wire extending from the proximal end of the stent delivery system toward the distal end, and being connected to the retractable distal sheath at said distal end for retracting the retractable distal sheath proximally such that the retracting means moves axially with respect to the inner core, whereby when the retracting pull back wire is retracted the retractable distal sheath is retracted freeing the stent for delivery.

\* \* \* \* \*